United States Patent
Laroche et al.

(10) Patent No.: US 10,913,695 B2
(45) Date of Patent: Feb. 9, 2021

(54) ZEOLITE ADSORBENTS, PREPARATION PROCESS THEREFOR AND USES THEREOF

(71) Applicants: IFP ENERGIES NOUVELLES, Rueil-Malmaison (FR); ARKEMA FRANCE, Colombes (FR)

(72) Inventors: Catherine Laroche, Vernaison (FR); Ludivine Bouvier, Orthez (FR); Javier Perez-Pellitero, Lyons (FR)

(73) Assignees: IFP ENERGIES NOUVELLES; ARKEMA FRANCE

( * ) Notice: Subject to any disclaimer, the term of this patent is extended or adjusted under 35 U.S.C. 154(b) by 433 days.

(21) Appl. No.: 15/742,614

(22) PCT Filed: Jul. 8, 2016

(86) PCT No.: PCT/EP2016/066293
§ 371 (c)(1),
(2) Date: Jan. 8, 2018

(87) PCT Pub. No.: WO2017/005907
PCT Pub. Date: Jan. 12, 2017

(65) Prior Publication Data
US 2018/0201555 A1    Jul. 19, 2018

(30) Foreign Application Priority Data

Jul. 9, 2015  (FR) ..................... 15 56523

(51) Int. Cl.
| | |
|---|---|
| *B01J 20/18* | (2006.01) |
| *C07C 7/13* | (2006.01) |
| *C07C 29/76* | (2006.01) |
| *C07C 37/82* | (2006.01) |
| *B01J 20/30* | (2006.01) |
| *B01J 20/16* | (2006.01) |
| *B01J 29/08* | (2006.01) |
| *B01J 37/02* | (2006.01) |
| *B01J 37/30* | (2006.01) |
| *C07C 39/07* | (2006.01) |
| *C07C 15/02* | (2006.01) |
| *B01D 15/08* | (2006.01) |
| *B01J 20/04* | (2006.01) |
| *C07C 15/08* | (2006.01) |
| *C07C 209/86* | (2006.01) |
| *C07C 201/16* | (2006.01) |
| *C07C 211/50* | (2006.01) |
| *C07C 205/06* | (2006.01) |

(52) U.S. Cl.
CPC .............. *C07C 7/13* (2013.01); *B01D 15/08* (2013.01); *B01J 20/041* (2013.01); *B01J 20/16* (2013.01); *B01J 20/18* (2013.01); *B01J 20/186* (2013.01); *B01J 20/3085* (2013.01); *B01J 29/082* (2013.01); *B01J 37/0201* (2013.01); *B01J 37/30* (2013.01); *C07C 15/02* (2013.01); *C07C 15/08* (2013.01); *C07C 29/76* (2013.01); *C07C 37/82* (2013.01); *C07C 39/07* (2013.01); *B01D 2253/108* (2013.01); *B01D 2253/1085* (2013.01); *B01J 2229/10* (2013.01); *B01J 2229/18* (2013.01); *B01J 2229/30* (2013.01); *C07C 201/16* (2013.01); *C07C 205/06* (2013.01); *C07C 209/86* (2013.01); *C07C 211/50* (2013.01)

(58) Field of Classification Search
CPC . B01J 20/16; B01J 20/18; B01J 20/186; B01J 20/041; B01J 20/3085; B01J 2229/10; B01J 2229/18; B01J 2229/186; B01J 2229/30; B01J 29/082; B01J 37/30; B01J 37/0201; B01D 2253/108; B01D 2253/1085; B01D 15/08; C07C 29/76; C07C 15/08; C07C 15/02; C07C 37/82; C07C 39/07; C07C 7/13; C07C 209/86; C07C 201/16; C07C 205/06; C07C 211/50
USPC ............ 502/64, 69, 79, 400, 407, 411, 415; 585/804, 820, 825, 828, 831; 208/310 R, 208/310 Z
See application file for complete search history.

(56) References Cited

U.S. PATENT DOCUMENTS

| | | | |
|---|---|---|---|
| 2,985,589 A | 5/1961 | Broughton | |
| 3,558,730 A | 1/1971 | Neuzil | |
| 3,558,732 A | 1/1971 | Neuzil | |
| 3,626,020 A | 12/1971 | Neuzil | |
| 3,663,638 A | 5/1972 | Neuzil | |
| 3,686,342 A * | 8/1972 | Neuzil ..................... | C07C 7/13 585/828 |
| 3,706,813 A | 12/1972 | Neuzil | |
| 3,960,774 A | 6/1976 | Rosback | |
| 4,402,832 A | 9/1983 | Gerhold | |

(Continued)

FOREIGN PATENT DOCUMENTS

| | | |
|---|---|---|
| CN | 1347339 A | 5/2002 |
| CN | 1565718 | 1/2005 |

(Continued)

OTHER PUBLICATIONS

Taiwan Office Action for Taiwan Application No. 105121848, dated Sep. 10, 2019, 5 pages, 2019.
International Search Report and Written Opinion for International Application No. PCT/EP2016/066293, dated Oct. 18, 2016 (11 pages).

(Continued)

*Primary Examiner* — Elizabeth D Wood
(74) *Attorney, Agent, or Firm* — RatnerPrestia

(57) ABSTRACT

The present invention relates to zeolite adsorbents based on agglomerated zeolite X crystals comprising barium, potassium and sodium. These adsorbents find applications in the separation of aromatic C8 isomer fractions and especially xylene.

18 Claims, 1 Drawing Sheet

(56) References Cited

U.S. PATENT DOCUMENTS

| | | | |
|---|---|---|---|
| 4,498,991 | A | 2/1985 | Oroskar |
| 5,284,992 | A | 2/1994 | Hotier et al. |
| 5,629,467 | A | 5/1997 | Hotier et al. |
| 6,284,021 | B1* | 9/2001 | Lu ................. B01D 53/02 95/102 |
| 7,011,695 | B2 | 3/2006 | Moreau et al. |
| 7,452,840 | B2 | 11/2008 | Plee et al. |
| 7,785,563 | B2 | 8/2010 | Ryoo et al. |
| 7,820,869 | B2 | 10/2010 | Priegnitz et al. |
| 8,283,274 | B2 | 10/2012 | Cheng et al. |
| 8,388,735 | B2 | 3/2013 | Bedard et al. |
| 8,431,764 | B2 | 4/2013 | Hurst et al. |
| 8,557,028 | B2 | 10/2013 | Hurst et al. |
| 8,603,433 | B2 | 12/2013 | Hurst et al. |
| 8,603,434 | B2 | 12/2013 | Hurst et al. |
| 8,609,925 | B2 | 12/2013 | Cheng et al. |
| 8,735,643 | B2* | 5/2014 | Bouvier ............... B01J 20/186 585/820 |
| 9,242,237 | B2 | 1/2016 | Monereau |
| 9,463,446 | B2 | 10/2016 | Kwon et al. |
| 9,707,539 | B2 | 7/2017 | Bats et al. |
| 9,914,109 | B2 | 3/2018 | Laroche et al. |
| 9,919,289 | B2 | 3/2018 | Bouvier et al. |
| 10,112,173 | B2 | 10/2018 | Bouvier et al. |
| 2009/0326308 | A1 | 12/2009 | Kulprathipanja et al. |
| 2011/0105301 | A1* | 5/2011 | Wang ................. B01J 20/186 502/62 |
| 2011/0184165 | A1* | 7/2011 | Bouvier ......... B01J 20/28069 536/127 |
| 2015/0105600 | A1 | 4/2015 | Whitchurch et al. |
| 2015/0306565 | A1* | 10/2015 | Bouvier .................. C07C 7/13 568/758 |
| 2016/0009614 | A1* | 1/2016 | Laroche ............... B01J 20/183 585/828 |

FOREIGN PATENT DOCUMENTS

| | | |
|---|---|---|
| CN | 1267185 | 8/2006 |
| FR | 2789914 A1 | 8/2000 |
| FR | 290398 | 1/2008 |
| FR | 2999098 | 6/2014 |
| TW | 201427768 A | 7/2014 |
| TW | 201509519 A | 5/2015 |
| TW | 201515700 A | 5/2015 |
| TW | 201742669 A | 12/2017 |
| WO | 2013106816 | 7/2013 |

OTHER PUBLICATIONS

Ruthven, "Principles of Adsorption and Adsorption Processes", John Wiley & Sons, (1984), Chapters 8 and 9, and pp. 326 and 407.

Zeolite Molecular Sieves by D.W. Breck, John Wiley and Sons, New York, (1973), pp. 314-315.

Mazotti, Storti and Morbidelli in Robust Design of Countercurrent Adsorption Separation Processes: 2. Multicomponent Systems, AlChE Journal Nov. 1994 vol. 40, No. 11.

Verboekend, D. et al., "Synthesis, characterisation, and catalytic evaluation of hierachical faujasite zeolites: milestones, challenges, and future directions," Issue 12, 2016, 51 pages, Chemical Society Reviews.

Notice of Allowance for U.S. Appl. No. 15/742,636, dated Apr. 17, 2020, 7 pages.

Taiwan Office Action for Taiwan Application No. 105121713, dated Sep. 16, 2019 with English Search Report, 8 pages.

Non Final Office Action for U.S. Appl. No. 15/742,636, dated Jun. 26, 2019, 19 pages.

Inayat et al. (Angew. Chem. Int. Ed., (2012), 51, 1962-1965).

Verboekend et al., "Hierarchical Y and USY Zeolites Designed by Post-Synthetic Strategies", Advanced Functional Materials, 2012, vol. 22, pp. 916-928.

Chinese Office Action for Chinese Application No. 201680040332. X, dated May 18, 2020 with translation, 19 pages.

* cited by examiner

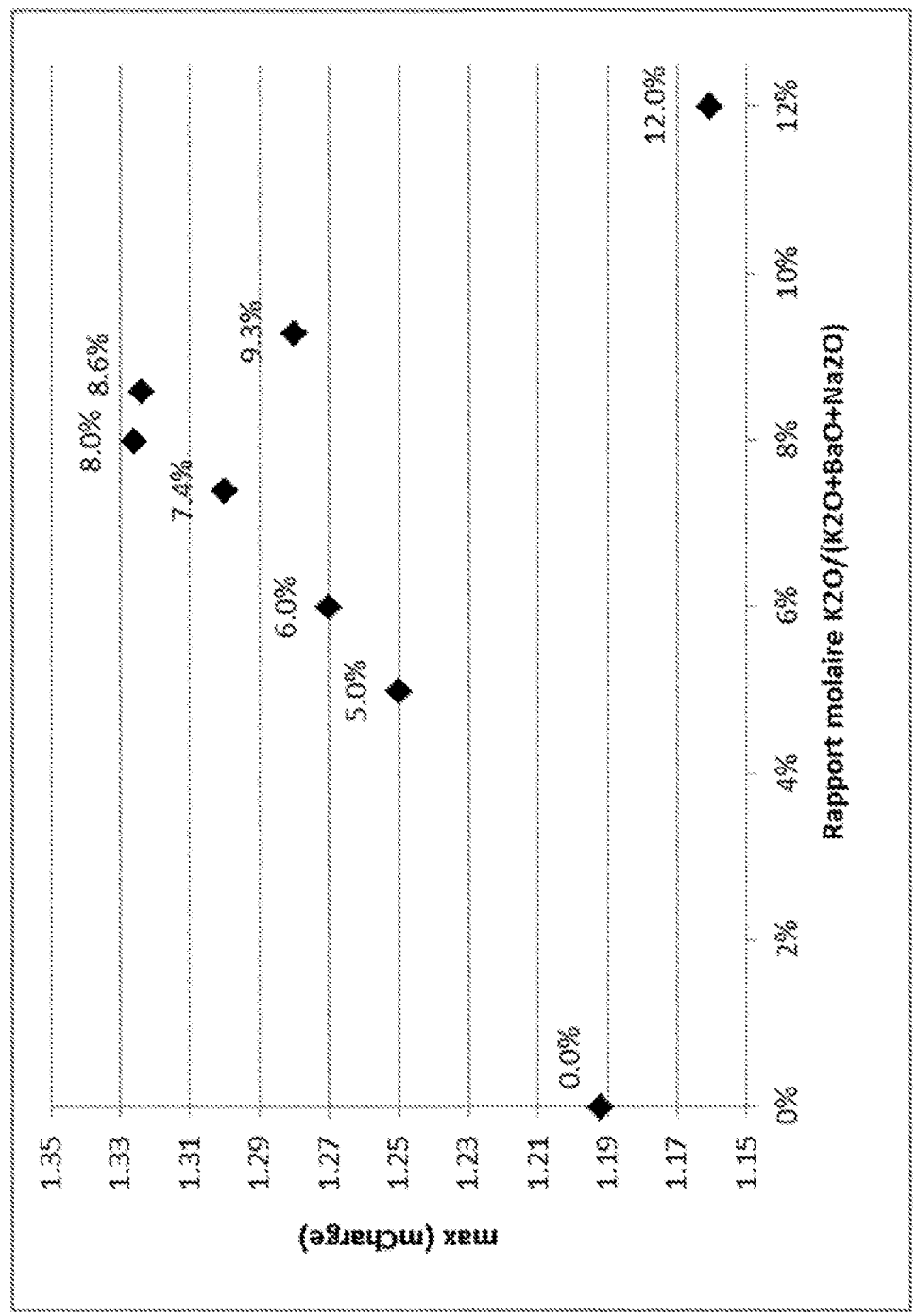

ZEOLITE ADSORBENTS, PREPARATION PROCESS THEREFOR AND USES THEREOF

CROSS-REFERENCE TO RELATED APPLICATIONS

This is the national phase of International Application No. PCT/EP2016/066293, filed Jul. 8, 2016, which claims priority to French Application No, 1556523, filed Jul. 9, 2015. The disclosure of each of these applications is incorporated herein by reference in its entirety for all purposes.

FIELD OF THE INVENTION

The invention relates to adsorbents based on agglomerated crystals of zeolite X comprising barium and potassium, to the process for preparing them and to the uses thereof.

These adsorbents may be used more particularly for the liquid-phase or gas-phase production of very pure para-xylene from an aromatic hydrocarbon feed containing isomers bearing 8 carbon atoms.

BACKGROUND OF THE INVENTION

It is known in the prior art that adsorbents comprising crystalline aluminosilicates may be used for separating certain hydrocarbons from mixtures containing them. In the field of separating aromatic hydrocarbons and in particular separating aromatic C8 isomers, it is generally acknowledged that the use of particular cations in the cationic sites of crystalline zeolite aluminosilicates improves the selectivity of the zeolite for one of the aromatic C8 isomers. This differential adsorption within the zeolite allows separation of the various aromatic C8 isomers, which is used industrially for the production of very pure para-xylene from an aromatic hydrocarbon feed containing isomers bearing 8 carbon atoms.

Thus, the use of zeolite adsorbents constituted of zeolites X or Y comprising, besides sodium cations, barium, potassium or strontium ions, alone or as mixtures, for selectively adsorbing para-xylene in the liquid phase in an aromatic hydrocarbon mixture, is well know in the prior art.

U.S. Pat. Nos. 3,558,730, 3,558,732, 3,626,020, 3,663, 638 and 3,960,774 show that zeolite adsorbents comprising aluminosilicates of faujasite (FAU) structure based on sodium and barium or based on sodium, barium and potassium, are effective for separating para-xylene present in aromatic C8 fractions (fractions comprising aromatic hydrocarbons bearing 8 carbon atoms). The above adsorbents are preferably used as adsorption agents in liquid-phase processes, especially of simulated counter-current type, similar to those described in U.S. Pat. No. 2,985,589 and which apply, inter alia, to aromatic C8 fractions.

However, in general, the adsorption properties of zeolites for aromatic hydrocarbons bearing 8 carbon atoms (xylenes and ethylbenzene) vary very finely as a function of the size and shape of the pores and also of the position of the cations within the structure which have an influence both on the electrostatic field present within the zeolite and on the form of the accessible volume in the pores. Other parameters, such as the polarizability of the cations and molecules or the flexibility of the structure, may also have an influence. It is thus extremely difficult to predict theoretically and with precision the adsorption characteristics of a zeolite with respect to aromatic hydrocarbons bearing 8 carbon atoms.

To improve the adsorption selectivity of zeolites having the faujasite structure for aromatic C8 isomers, many studies have mentioned the influence of the Si/Al ratio of the zeolite, the nature of the exchange cations, and also the water content thereof. Similarly, it is very difficult to predict the degree of improvement since these factors exert combined actions on the adsorption characteristics of zeolites. In particular, it is difficult to predict the impact of the relative proportion of barium ions, and potassium in the case of a zeolite of faujasite (FAU) structure based on barium and potassium, and more precisely in the case of a zeolite of faujasite (FAU) structure of type X, based on barium and potassium.

Patent FR 2 903 978 teaches that potassium ions may represent up to ⅓ of the exchangeable sites occupied by barium and potassium, but said patent does not illustrate any adsorbent containing potassium and does not give any teaching that makes it possible to anticipate the impact of potassium on the adsorption selectivities.

U.S. Pat. Nos. 8,283,274 and 8,557,028 describe adsorbents with potassium weight contents of between 0.25% and 0.9% by weight, corresponding to $K_2O/(BaO+K_2O+Na_2O)$ mole ratios of between 1.3% and 4.5%. U.S. Pat. No. 8,557,028 claims adsorbents with potassium weight contents of between 0.9% and 1.5%, equivalent to $K_2O/(BaO+K_2O+Na_2O)$ mole ratios of between 4.5% and 7.5%. The examples of the latter patent show that the productivity is improved with adsorbents that have potassium contents of between 0.5% and 0.7% by weight, equivalent to $K_2O/(BaO+K_2O+Na_2O)$ mole ratios of 2.5% and 3.5%. Patent CN 1267185 describes adsorbents with $BaO/K_2O$ mole ratios of between 10 and 40 corresponding to $K_2O/(BaO+K_2O+Na_2O)$ mole ratios of between 2.4% and 9.1%.

The recent patent US 2015/0 105 600 describes an adsorbent based on zeolite X, barium and potassium, with a $K_2O/(BaO+K_2O+Na_2O)$ mole ratio of between 15% and 40%.

The synthesis of zeolites leads to crystals (generally in powder form) whose use at the industrial scale is particularly difficult (substantial losses of feed during the manipulations). The agglomerated forms of these crystals are thus preferred, in the form of grains, yarns and other agglomerates, these said forms possibly being obtained by extrusion, pelleting and other agglomeration techniques known to those skilled in the art. These agglomerates do not have the drawbacks inherent in pulverulent materials.

These agglomerates, whether they are in the form of platelets, beads, extrudates or the like, are generally formed from zeolite crystals, which constitute the active element (in the sense of adsorption) and of a binder intended to ensure the cohesion of the crystals in the form of agglomerates and to give them sufficient mechanical strength to withstand the vibrations and movements to which they are subjected during the operations for separation of the isomers of the C8 aromatic fractions. However, the adsorption properties of these agglomerates are obviously reduced relative to the crystal powder, on account of the presence of agglomeration binder that is inert with respect to adsorption.

Various means have already been proposed to overcome this drawback of the agglomeration binder being inert with respect to adsorption performance, among which is the transformation of all or at least part of the agglomeration binder into zeolite that is active from the point of view of adsorption. This operation is now well known to those skilled in the art, for example under the name "zeolitization". To perform this operation easily, zeolitizable binders are used, usually clays belonging to the kaolinite family, and preferably calcined beforehand at temperatures generally between 500° C. and 700'C.

Patent application FR 2789 914 describes, for example, a process for manufacturing zeolite X agglomerates, with an Si/Al ratio of between 1.15 and 1.5, containing barium and optionally potassium. The agglomerates thus obtained, after zeolitization of the binder, have, from the point of view of adsorption of para-xylene contained in aromatic C8 fractions, improved properties relative to adsorbents prepared from the same amount of zeolite X and binder, but whose binder is not zeolitized.

The important factors that influence the performance of an adsorption separation process especially encompass the adsorption selectivity, the adsorption capacity and the matter transfer kinetics which defines the rate of adsorption and desorption of the various compounds. The adsorbent must thus have good matter transfer properties so as to ensure a sufficient number of theoretical plates to achieve efficient separation of the mixed species, as indicated by Ruthven in the publication entitled "Principles of Adsorption and Adsorption Processes", John Wiley & Sons, (1984), pages 326 and 407. Ruthven indicates (ibid., page 243) that, in the case of an agglomerated adsorbent, the overall matter transfer depends on the addition of the intra-crystalline diffusional resistance and of the inter-crystalline diffusional resistance. The intra-crystalline diffusional resistance is proportional to the square of the radii of the crystals and inversely proportional to the diffusivity of the intra-crystalline molecules.

The inter-crystalline diffusional resistance (also known as the macropore resistance) is itself proportional to the square of the radii of the agglomerates and inversely proportional to the diffusivity of the molecules in the macropores. For a given zeolite structure, a given agglomerate size and a given operating temperature, the diffusivities are fixed, and the only way of improving the matter transfer consists in reducing the diameter of the crystals. A gain in the overall transfer will thus be obtained by reducing the size of the crystals.

Consequently, a person skilled in the art expects agglomerated zeolite adsorbents that have both good xylene adsorption capacity and good selectivity for para-xylene to have very good xylene separation properties when they are prepared from small zeolite crystals in liquid-phase processes for separating para-xylene contained in aromatic C8 fractions, for example of the simulated counter-current type. It is, however, impossible for a person skilled in the art to define in principle or theoretically and with precision the adsorption characteristics of an FAU zeolite, especially of X type, having a particular barium and potassium composition, with respect to aromatic hydrocarbons bearing 8 carbon atoms.

The object of the present invention is to provide novel adsorbents based on zeolite X comprising barium, potassium and sodium and having a particular composition of barium, potassium and sodium, which is optimum for maximizing the production efficiency of the process for separating para-xylene contained in aromatic C8 fractions. The present invention also proposes a process for separating xylenes using an adsorbent based on zeolite X having a particular composition of barium, potassium and sodium, allowing the production of para-xylene in high purity with improved production efficiency starting with an aromatic hydrocarbon feed containing isomers bearing 8 carbon atoms.

SUMMARY OF THE INVENTION

The Invention relates to a zeolite adsorbent comprising zeolite X crystals and comprising barium, potassium and sodium, in which the $K_2O/(K_2O+BaO+Na_2O)$ mole ratio (of the species in oxide form) is between 8.0% and 8.6%, preferably between 8.2% and 8.4%. In an advantageous variant, the $K_2O/(K_2O+BaO+Na_2O)$ mole ratio is equal to 8.3%. In the present invention, the $K_2O/(K_2O+BaO+Na_2O)$ mole ratio is expressed as percent of the number of moles of $K_2O$ relative to the sum of the number of moles of $(K_2O+BaO+Na_2O)$.

The content of sodium oxide $Na_2O$ is advantageously less than 0.3% by weight and preferably less than 0.2% by weight relative to the total mass of the adsorbent.

The total content of alkali metal or alkaline-earth metal ion oxides other than barium oxide BaO, potassium oxide $K_2O$ and sodium oxide $Na_2O$ is advantageously less than 1% by weight, preferably between 0 and 0.5% by weight and very preferably between 0 and 0.3% by weight, relative to the total mass of the adsorbent.

The zeolite X crystals advantageously have an Si/Al atomic ratio of between 1.00 and 1.50, preferably between 1.05 and 1.50 and more preferably between 1.10 and 1.50.

The number mean diameter of the zeolite X crystals is less than or equal to 1.5 µm, preferably between 0.1 µm and 1.2 µm, more preferably between 0.1 µm and 1.0 µm.

The loss on ignition of the adsorbent according to the invention, measured at 950° C. according to standard NF EN 196-2, is advantageously between 4.0% and 7.7%, preferably between 4.5% and 6.5% and very preferably between 4.8% and 6% by weight.

The number mean diameter of the adsorbent according to the invention may be between 0.2 mm and 2 mm, in particular between 0.2 mm and 0.8 mm and preferably between 0.2 mm and 0.65 mm.

The invention also relates to a process for preparing an adsorbent as described above, comprising at least the steps of:
  a) agglomerating a powder of zeolite X crystals with a binder, and forming, followed by drying and calcination,
  b) optional zeolitization of the binder,
  c) cation exchange of the agglomerate by placing in contact with a solution of barium ions, or of potassium ions, or of barium ions and potassium ions,
  d) cation exchange with potassium when the exchange step c) is performed with a solution of barium ions alone, or cation exchange with barium when the exchange step c) is performed with a solution of potassium ions alone,
  e) followed by washing and drying of the product thus treated,
  f) activation of the zeolite adsorbent thus obtained.

Preferably, the process for preparing the adsorbent involves a step b) of zeolitization of the binder.

Preferably, the solution(s) of barium ions, or potassium ions, or barium and potassium ions of steps c) and d) have a concentration of between 0.2M and 2M.

The invention also relates to an adsorbent as described previously, which may be obtained according to the above preparation process.

The invention also relates to the use of said adsorbent according to the invention in processes for:
  separating aromatic C8 isomer fractions and especially xylenes,
  separating substituted toluene isomers such as nitrotoluene, diethyltoluene, toluenediamine and the like,
  separating cresols,
  separating polyhydric alcohols,
and especially for separating para-xylene from aromatic isomer fractions bearing 8 carbon atoms.

The invention also relates to a process for recovering para-xylene from aromatic hydrocarbon isomer fractions containing 8 carbon atoms, in the liquid phase, by adsorption of para-xylene using said adsorbent according to the invention in the presence of a desorbent, preferably chosen from toluene and para-diethylbenzene.

Said process may be of the simulated moving bed type, preferably with simulated counter-current.

The invention also relates to a process for recovering para-xylene from isomer fractions of aromatic hydrocarbons containing 8 carbon atoms, in the gaseous phase, by adsorption of para-xylene using said adsorbent according to the invention in the presence of a desorbent, preferably chosen from toluene and para-diethylbenzene.

The invention also relates to a process for separating polyhydric alcohols using said adsorbent according to the invention.

The invention also relates to a process for separating substituted toluene isomers such as nitrotoluene, diethyltoluene and toluenediamine, using said adsorbent according to the invention.

Finally, the invention relates to a process for separating cresols using said adsorbent according to the invention.

In the text hereinbelow, and unless otherwise indicated, the limits of a range of values are included in that range, especially in the expressions "between" and "ranging from . . . to . . . ".

BRIEF DESCRIPTION OF THE FIGURE

FIG. 1: Plot of $K_2O/(K_2O+BaO+Na_2O)$ mole ratios vs max (mFeed) as described in Example 1.

DETAILED DESCRIPTION OF THE INVENTION

A first subject of the present invention is thus zeolite adsorbents based on zeolite X. These adsorbents are particularly suitable for use in a process for separating paraxylene in the liquid phase, preferably of simulated countercurrent type.

Thus, the present invention relates to a zeolite adsorbent comprising zeolite X crystals and comprising barium, potassium and sodium, in which the $K_2O/(K_2O+BaO+Na_2O)$ mole ratio is between 8.0% and 8.6%, preferably between 8.2% and 8.4%, and more preferably is equal to 8.3%.

The adsorbents according to the invention may also comprise a non-zeolite phase, i.e. a non-crystalline phase that is essentially inert with respect to adsorption. In the case where the adsorbent according to the invention comprises a non-zeolite phase, the $K_2O/(K_2O+BaO+Na_2O)$ mole ratio takes into account the oxides included in said non-zeolite phase.

The content of sodium oxide $Na_2O$ in the adsorbent according to the invention is advantageously less than 0.3% by weight and preferably less than 0.2% by weight relative to the total mass of the adsorbent.

The total content of alkali metal or alkaline-earth metal ion oxides other than barium oxide BaO, potassium oxide $K_2O$ and sodium oxide $Na_2O$ in the adsorbent according to the invention is advantageously less than 1% by weight, preferably between 0 and 0.5% by weight and very preferably between 0 and 0.3% by weight, relative to the total mass of the adsorbent.

The zeolite adsorbent according to the present invention is an adsorbent based on FAU zeolite crystals of X type. The term "zeolite X" means zeolites whose Si/Al atomic ratio is between 1.00 and 1.50, preferably between 1.05 and 1.50, and more preferably between 1.10 and 1.50.

Among the zeolites X, it is now commonly accepted to acknowledge two sub-groups known as zeolites LSX and zeolites MSX. Zeolites LSX have an Si/Al atomic ratio equal to about 1 and zeolites MSX have an Si/Al atomic ratio of between about 1.05 and about 1.15.

In the zeolite adsorbent of the present invention, and according to a preferred embodiment, the term "FAU zeolite of X type" means FAU zeolites of X type defined above, these said zeolites being hierarchically porous, i.e. hierarchically porous type X zeolites (or zeolite HPX), hierarchically porous zeolites of MSX type (or HPMSX) and hierarchically porous zeolites of LSX type (or HPLSX), and more particularly hierarchically porous FAU zeolites with an Si/Al atomic ratio of between 1.00 and 1.50, preferably between 1.05 and 1.50, more preferably between 1.05 and 1.40 and even more preferably between 1.15 and 1.40.

The invention also comprises zeolite adsorbents comprising mixtures of two or more hierarchically porous FAU zeolites as have just been defined.

The term "hierarchically porous zeolite" means a zeolite simultaneously having micropores and mesopores, in other words a zeolite that is both microporous and mesoporous. The term "mesoporous zeolite" means a zeolite whose microporous zeolite crystals have, in conjunction with microporosity, internal cavities of nanometric size (mesoporosity), which are readily identifiable by means of transmission electron microscopy (TEM), as described, for example, in U.S. Pat. No. 7,785,563: observation by transmission electron microscopy (TEM) makes it possible to check whether the zeolite crystals are filled zeolite crystals (i.e. not mesoporous) or aggregates of filled zeolite crystals or mesoporous crystals or aggregates of mesoporous crystals.

The crystalline structure of the type X FAU zeolite in the zeolite adsorbent of the present invention is identifiable by X-ray diffraction (known to those skilled in the art by the abbreviation XRD).

According to a preferred embodiment, the zeolite adsorbent has an Si/Al atomic ratio of between 1.00 and 2.00, preferably between 1.00 and 1.80, more preferably between 1.15 and 1.80, and even more preferably between 1.15 and 1.60.

In the present document, the term "number mean diameter" or "size" is used for the zeolite crystals and for the zeolite agglomerates. The method for measuring these magnitudes is explained later in the description. According to a preferred embodiment of the present invention, the number mean diameter of the zeolite X crystals is less than or equal to 1.5 µm, preferably between 0.1 µm and 1.2 µm and more preferably between 0.1 µm and 1.0 µm.

The zeolite adsorbent of the invention is preferably in the form of an agglomerate, i.e. it is constituted of zeolite crystals and of at least one non-zeolite phase which may comprise an agglomeration binder allowing cohesion of the crystals. Thus, the zeolite adsorbent of the invention is often referred to as an "agglomerate" in the present description.

The mass fraction of zeolite X in the adsorbent according to the present invention may be at least 80% by weight relative to a total weight of the adsorbent, preferably at least 90%, this mass fraction possibly being up to 100% and typically up to 99.5% by weight.

According to a preferred embodiment, the zeolite adsorbent according to the invention has a loss on ignition measured at 950° C. according to standard NF EN 196-2 of between 4.0% and 7.7%, preferably between 4.5% and 6.5% and advantageously between 4.8% and 6%.

The zeolite adsorbent according to the present invention preferentially has a mechanical strength generally greater than or equal to 1.8 MPa, typically greater than or equal to 2.1 MPa. This mechanical strength is measured via the Shell method series SMS1471-74 adapted for agglomerates smaller than 1.6 mm in size.

The adsorption capacity is itself measured by measuring the micropore volume of the adsorbent evaluated from the Dubinin-Raduskevitch equation by adsorption of nitrogen ($N_2$) at a temperature of 77 K, after degassing under vacuum at 300° C. for 16 hours. The micropore volume of the zeolite adsorbents of the invention was thus measured as being greater than 0.250 $cm^3/g$, typically in a range from 0.256 $cm^3/g$ to 0.288 $cm^3/g$.

According to another aspect, the invention relates to a process for preparing zeolite agglomerates as have just been defined, this process comprising at least the steps of:
  a) agglomerating zeolite X crystals (powder) with a binder, and forming agglomerate, followed by drying and calcination,
  b) optional zeolitization of said binder, preferably via the action of an alkaline basic solution,
  c) cation exchange of the agglomerate by placing in contact with a solution of barium ions, or of potassium ions, or of barium ions and potassium ions,
  d) cation exchange with potassium when the exchange step c) is performed with a solution of barium ions alone, or cation exchange with barium when the exchange step c) is performed with a solution of potassium ions alone,
  e) followed by washing and drying of the product thus treated,
  f) activation of the zeolite agglomerate.

Preferably, the process for preparing the zeolite agglomerates involves a step b) of zeolitization of the binder.

Preferably, the solution(s) of barium ions, or potassium ions, or barium and potassium ions of steps c) and d) have a concentration of between 0.2M and 2M.

The size of the zeolite X crystals used in step a) is measured by observation with a scanning electron microscope (SEM) or by observation with a transmission electron microscope (TEM). This SEM or TEM observation also makes it possible to confirm the presence of non-zeolite phase comprising, for example, the binder or the residual binder not converted during the optional zeolitization step or any other amorphous phase in the agglomerates.

According to one embodiment, the zeolite X used in step a) comprises, and preferably is, a hierarchically porous type X FAU zeolite. Crystals of hierarchically porous type X FAU zeolite with a large outer surface area may be obtained according to various methods known to those skilled in the art, for example according to the synthesis described by Inayat et al. (*Angew. Chem. Int. Ed.*, (2012), 51, 1962-1965).

It is also possible to prepare said crystals by synthesis by seeding and/or by adjusting the synthesis operating conditions such as the $SiO_2/Al_2O_3$ ratio, the sodium content and the alkalinity of the synthetic mixture or alternatively according to conventional processes for post-treatment of type X FAU zeolite crystals that are known to those skilled in the art.

The post-treatment processes generally consist in eliminating atoms from the already-formed zeolite network, either via one or more acid treatments that dealuminate the solid, these treatments being followed by one or more washes with sodium hydroxide (NaOH) in order to remove the aluminous residues formed, as described, for example, by D. Verboekend et al. (*Adv. Funct. Mater.*, 22, (2012), pages 916-928), or alternatively via treatments that combine the action of an acid and that of a structuring agent which improve the efficacy of the acid treatment, as described, for example, in patent application WO 2013/106 816.

The agglomeration and forming (step a) may be performed according to any technique known to those skilled in the art, such as extrusion, compacting, agglomeration, and the like. The proportions of agglomeration binder, optionally zeolitizable (see the definition later), and of zeolite(s) used are typically those of the prior art, i.e. from 5 parts to 20 parts by weight of binder per 95 parts to 80 parts by weight of zeolite. The agglomerates derived from step a), whether in the form of beads, extrudates or the like, generally have a number mean diameter (or their largest dimension when they are not spherical) of between 0.2 mm and 2 mm, in particular between 0.2 mm and 0.8 mm and preferably between 0.2 mm and 0.65 mm.

On conclusion of step a), the finest agglomerated particles may be removed by cycloning and/or screening and the excessively coarse particles by screening or crushing, for example in the case of extrudates.

The agglomeration binder used in step a) may be zeolitizable. It then contains at least 80%, preferably at least 90%, more preferably at least 95%, more particularly at least 96% by weight of zeolitizable clay and may also contain other mineral binders such as bentonite, attapulgite, and the like. The term "zeolitizable clay" means a clay or a mixture of clays that can be converted into zeolite material (i.e. material that is active in the sense of adsorption), usually via the action of an alkaline basic solution. The zeolitizable day generally belongs to the family of kaolins, kaolinites, nacrites, dickites, halloysite and/or metakaolins. Kaolin is preferred and is most commonly used.

Other clays especially such as sepiolite or attapulgite may also be used.

In all cases, the clays may be used in their crude form or may be subjected beforehand to one or more treatments chosen, for example, from calcination, acid treatment, chemical modification, and the like.

The zeolite X powder used in step a) may be derived from the synthesis of zeolite X crystals predominantly, or even exclusively, comprising sodium cations, for example zeolites NaX, but it would not constitute a departure from the context of the invention to use a powder that has undergone one or more cation exchangers, after its synthesis and before its use in step a).

During step a), besides the zeolite X powder and the binder, one or more additives may also be added, for example additives intended to facilitate the agglomeration or to improve the hardening of the agglomerates formed, such as lignin, starch, carboxymethylcellulose, and other additives known to those skilled in the art. Silica may also be added. The optional source of silica may be of any type known to a person skilled in the art, who is a specialist in zeolite synthesis, for example colloidal silica, diatomaceous earths, perlite, fly ash, sand, or any other form of solid silica.

After the drying in step a), calcination is conducted at a temperature generally between 500° C. and 600° C. In the case where the forming is performed with a zeolitizable clay, this step makes it possible to transform the zeolitizable clay, typically kaolin, into metakaolin, which may subsequently be converted into zeolite during the zeolitization step (step b)). The principle thereof is presented in "Zeolite Molecular Sieves" by D. W. Breck, John Wiley and Sons, New York, (1973), pages 314-315.

Zeolitization of the agglomeration binder is performed according to any method known to those skilled in the art and may be performed, for example, by immersing the product from step a) into an alkaline basic solution, generally an aqueous solution, for example an aqueous solution of sodium hydroxide and/or of potassium hydroxide.

As a general rule, the concentration of the alkaline zeolitization solution is preferably between 0.5M and 5M. The zeolitization is preferably performed hot, at a temperature above room temperature, and typically at temperatures of the order of 80° C. to 100° C., for example between room temperature (i.e. about 20° C.) and the boiling point of the alkaline zeolitization solution. The duration of the zeolitization process is generally between a few tens of minutes and a few hours, preferably between about 1 hour and 8 hours.

Steps c) and d) of exchange with barium and/or potassium of the cations of the zeolite X are performed according to the standard methods known to those skilled in the art, and usually by placing the agglomerates derived from step a) or from step b) in contact with a salt, such as barium chloride ($BaCl_2$) for the barium exchange and/or potassium chloride (KCl) for the potassium exchange, in aqueous solution at a temperature between room temperature and 100° C., and preferably between 80° C. and 100° C. To rapidly obtain low sodium oxide contents, i.e. contents below 1%, it is preferred to work with a large excess of barium and/or potassium ions relative to the cations of the zeolite that it is desired to exchange, typically an excess of the order of 10 to 12, advantageously by performing successive exchanges.

In order to achieve the $K_2O/(K_2O+BaO+Na_2O)$ mole ratio between 8.0% and 8.6%, one or more ionic exchange(s) is (are) performed by using barium ions aqueous solutions and potassium ions aqueous solutions, for example barium chloride and potassium chloride, at concentrations typically of between 0.05M and 1.5M, preferably of between 0.1M and 1.2M.

According to one specific embodiment, at least one exchange is performed by using a barium ions and potassium ions aqueous solution (corresponding to step c)). In this embodiment, step d) of the process according to the present application is not realized. This embodiment is the preferred embodiment.

According to another embodiment, at least one ionic exchange is firstly performed by using a barium ions aqueous solution (corresponding to step c)), and at least one ionic exchange is then performed by using a potassium ions aqueous solution (corresponding to step d)).

According to another embodiment, at least one ionic exchange is performed by using a potassium ions aqueous solution (corresponding to step c)), and at least one ionic exchange is then performed by using a potassium ions aqueous solution (corresponding to step d)).

Each exchange step may be performed one or more times.

The exchange(s) are performed according to the standard methods known to those skilled in the art, for example at temperatures between room temperature (about 20° C.) and 100° C., preferably between 80° C. and 100° C., generally at atmospheric pressure. The duration of the exchange step is generally between a few minutes and a few hours, preferably between about 30 minutes and 3 hours.

The adjustment of the $K_2O/(K_2O+BaO+Na_2O)$ mole ratio is achieved according to the standard methods known to those skilled in the art, and for example by performing one exchange with a large excess of barium ions in order to quickly obtain low contents of sodium oxide, i.e. less than 1%, preferably less than 0.3%, and then by performing another exchange thanks to a potassium ions aqueous solution containing the necessary molar quantity of potassium ions to achieve the targeted $K_2O/(K_2O+BaO+Na_2O)$ mole ratio.

As indicated previously, it is also possible to agglomerate in step a) zeolite X powder already containing potassium ions (pre-exchange of the cations present in the starting zeolite X, typically sodium cations, with potassium ions before step a)) and optionally to dispense with the potassium exchanges during steps c) and/or d).

Washing is then performed, generally and preferably with water, followed by drying of the agglomerate thus obtained.

The activation that follows the drying is performed conventionally, according to the methods known to those skilled in the art, for example at a temperature generally between 100° C. and 400° C., preferably between 200° C. and 300° C. The aim of this activation step f) is to set the water content, and also the loss on ignition of the adsorbent in an optimum manner for the intended use. The process is generally performed by thermal activation, which is preferentially performed at between 200° C. and 300° C. for a time determined as a function of the desired water content and the desired loss on ignition, typically from 1 to 6 hours.

The present invention also relates to the uses of the zeolite adsorbents described above as adsorption agents that can advantageously replace the adsorption agents described in the literature for the uses listed below:

separation of aromatic C8 isomer fractions and especially of xylenes,
separation of substituted toluene isomers such as nitrotoluene, diethyltoluene, toluenediamine, and the like,
separation of cresols,
separation of polyhydric alcohols, such as sugars.

The invention relates especially to a process for recovering para-xylene in high purity from aromatic isomer fractions bearing 8 carbon atoms, which consists in using, as para-xylene adsorption agent, a zeolite adsorbent according to the invention, performed in liquid-phase processes but also in gas-phase processes. The term "para-xylene of high purity" means a product that is suitable for use in the production of terephthalic acid or dimethyl terephthalate, i.e. a purity of at least 99.5% by weight, preferably at least 99.7% by weight, preferably at least 99.8% by weight and even more preferably at least 99.9% by weight. The purity of the para-xylene may be determined via chromatographic methods. A gas chromatography method that may be used both for determining the purity of the para-xylene and the specific amounts of impurities is the ASTM D-3798 method.

The desired product (para-xylene) may thus be separated out by preparative adsorption liquid chromatography (batchwise), and advantageously continuously on a simulated moving bed, i.e. with simulated counter-current or simulated co-current, and more particularly with simulated counter-current.

The process for recovering para-xylene according to the invention using the adsorbent described according to the invention has the advantage of maximizing the productivity, i.e. of maximizing the delivery rate of feed to be treated. This is particularly true under the following operating conditions for an industrial adsorption unit of simulated counter-current type:

number of beds: 6 to 30,
number of zones: at least 4 operating zones, each being located between a feed point and a withdrawal point, temperature between 100° C. and 250° C., preferably between 150° C. and 190° C., pressure of the industrial unit between the bubble pressure of xylenes at the process temperature and 3 MPa.

desorbent/feed delivery rate ratio of between 0.7 and 2.5, for example between 0.9 and 1.8 for a standalone adsorption unit and between 0.7 and 1.4 for an adsorption unit combined with a crystallization unit, recycling ratio (i.e. ratio of the mean recycling delivery rate (mean of the delivery rates of zones weighted by the number of beds per zone) to the feed delivery rate) of between 2.5 and 12, preferably between 3.5 and 6.

Reference may be made in this respect to the teaching of U.S. Pat. Nos. 2,985,589, 5,284,992 and 5,629,467.

The operating conditions of a simulated co-current industrial adsorption unit are generally the same as those of a unit functioning in simulated counter-current, with the exception of the recycling ratio, which is generally between 0.8 and 7. Reference may be made in this respect to U.S. Pat. Nos. 4,402,832 and 4,498,991.

The desorption solvent may be any desorbent known to those skilled in the art and whose boiling point is below that of the feed, such as toluene, but also a desorbent whose boiling point is above that of the feed, such as para-diethylbenzene (PDEB). The selectivity of the absorbents according to the invention for the adsorption of the para-xylene contained in aromatic C8 fractions is optimal when their loss on ignition measured at 950° C. is generally between 4.0% and 7.7%, preferably between 4.5% and 6.5% and very preferably between 4.8% and 6.0%.

Characterization Techniques
Particle Size of the Crystals:

The estimation of the number mean diameter of the zeolite X crystals used in step a) and of the zeolite X crystals contained in the agglomerates is performed by observation with a scanning electron microscope (SEM) or by observation with a transmission electron microscope (TEM).

In order to estimate the size of the zeolite crystals on the samples, a set of images is taken at a magnification of at least 5000. The diameter of at least 200 crystals is then measured using dedicated software, for example the Smile View software from the publisher LoGraMi. The accuracy is of the order of 3%.

Chemical Analysis of the Zeolite Adsorbents—Si/Al and $KO/(K_2O+BaO+Na_2O)$ Ratio:

A chemical elemental analysis of the final product obtained on conclusion of steps a) to f) described previously may be performed according to various analytical techniques known to those skilled in the art. Among these techniques, mention may be made of the chemical analysis technique by X-ray fluorescence as described in standard NF EN ISO 12677: 2011 on a wavelength-dispersive spectrometer (WDXRF), for example Tiger S8 from the company Brüker.

X-ray fluorescence is a non-destructive spectral technique exploiting the photoluminescence of atoms in the X-ray range, to establish the elemental composition of a sample. Excitation of the atoms generally by means of an X-ray beam or by bombardment with electrons generate specific radiations after return to the ground state of the atom. The X-ray fluorescence spectrum has the advantage of depending very little on the chemical combination of the element, which offers a precise quantitative and qualitative determination. After calibration for each oxide, a measuring uncertainty of less than 0.4% by weight is conventionally obtained. In the present invention, the barium, silicon and aluminium contents are preferably measured by the X-ray fluorescence method described above.

On the other hand, for the lighter elements in terms of atomic weight such as sodium or potassium present in the adsorbent, inductively coupled plasma-optical emission spectroscopy (ICP-OES) according to standard UOP 961-12 will be preferred for greater accuracy.

ICP is a method of analysis by atomic emission spectrometry whose source is a plasma generated by inductive coupling. This method is also commonly used to determine the contents of various elements such as silicon, aluminium, potassium, sodium and barium. In the present invention, the sodium and potassium contents are preferably measured via the ICP method according to standard UOP 961-12. In this case, sodium is obtained with a measuring uncertainty of less than 0.01% for the weight content of sodium oxide in the adsorbent and for potassium a measuring uncertainty of less than 0.02% for the weight content of potassium oxide in the adsorbent.

These elemental chemical analyses make it possible simultaneously to check the Si/Al atomic ratio of the zeolite in the agglomerate, and to check the quality of the ion exchange described in step c) and in step d). In the description of the present invention, the measuring uncertainty of the Si/Al atomic ratio is 0.05.

The quality of the ion exchange is associated with the number of moles of sodium oxide, $Na_2O$, remaining in the zeolite agglomerate after exchange. More precisely, the degree of exchange with barium ions is determined by the ratio between the number of moles of barium oxide, BaO, and the number of moles of the combination ($BaO+K_2O+Na_2O$). Similarly, the degree of exchange with potassium ions is determined by the ratio between the number of moles of potassium oxide, $K_2O$, and the number of moles of the combination ($BaO+K_2O+Na_2O$). BaO, $K_2O$ and $Na_2O$ are expressed in the form of oxides. The total degree of exchange with barium and potassium ions is estimated from the sum of the two degrees of exchange described previously, corresponding to the ratio between the sum of the number of moles of barium oxide and potassium oxide ($BaO+K_2O$) and the number of moles of the combination ($BaO+K_2O+Na_2O$). It should be noted that the contents of the various oxides are given as weight percentages relative to the total weight of the anhydrous zeolite adsorbent. In the description of the present invention, the measuring uncertainty regarding the $K_2O/(K_2O+BaO+Na_2O)$ mole ratio is 0.2%.

Particle Size of the Zeolite Adsorbents:

The determination of the number mean diameter of the zeolite adsorbents obtained on conclusion of the agglomeration and forming step a) is performed by analysis of the particle size distribution of an agglomerated sample by imaging according to standard ISO 13322-2:2006, using a conveyor belt for passing the sample before the objective lens of the camera.

The number mean diameter is then calculated from the particle size distribution by applying standard ISO 9276-2: 2001. In the present document, the term "number mean diameter" or "size" is used for the zeolite agglomerates. The accuracy is of the order of 0.01 mm for the size range of agglomerates of the invention.

Mechanical Strength of the Zeolite Adsorbents:

The technique for characterizing the representative mechanical crushing strength of the adsorbent in a bed or a reactor is the technique of characterizing the bulk mechanical strength as described in the Shell method series SMS1471-74 (Determination of Bulk Crushing Strength of Catalysts. Compression-Sieve Method), combined with the BCS Tester machine sold by the company Vinci Technologies. This method, initially intended for characterizing catalysts of 3 to 6 mm, is based on the use of a 425 μm screen which makes it possible especially to separate the fines created during crushing. The use of a 425 μm screen remains adapted to particles with a diameter of greater than 1.6 mm, but must be adapted according to the particle size of the zeolite adsorbents that it is desired to characterize. Standard ASTM D7084-04 which also describes a method for measuring the bulk crushing strength of catalysts (Determination of Bulk Crush Strength of Catalysts and Catalyst Carriers) defines the mesh size of the screen to be used as being equal to half the diameter of the catalyst particles to be characterized. The method envisages a preliminary step of screening the sample of catalysts or adsorbents to be characterized. If an amount equal to 10% by weight of the sample passes through the grate, a screen of smaller mesh size will be used.

The agglomerates of the present invention, generally in the form of beads or extrudates, generally have a number mean diameter or a length, i.e. greatest dimension in the case of non-spherical agglomerates, of between 0.2 mm and 2 mm, in particular between 0.2 mm and 0.8 mm and preferably between 0.2 mm and 0.65 mm. Consequently, a suitable screen such that less than 10% by weight of the sample passes through the grate during a preliminary screening step is used instead of the 425 μm screen mentioned in the standard Shell method SMS1471-74.

The measuring protocol is as follows: a sample of 20 cm$^3$ of agglomerated adsorbents, screened beforehand with the suitable screen and dried beforehand in a oven for at least 2 hours at 250° C. (instead of 300° C. mentioned in the standard Shell method SMS1471-74), is placed in a metal cylinder of known internal cross section. An increasing force is imposed in stages on this sample by means of a piston, through a bed of 5 cm$^3$ of steel beads so as best to distribute the force exerted by the piston on the adsorbent agglomerates (use of beads 2 mm in diameter for particles of spherical shape with a diameter strictly less than 1.6 mm). The fines obtained at the various pressure stages are separated by screening (with a suitable screen) and weighed.

The bulk crushing strength is determined by the pressure in megaPascals (MPa) for which the amount of cumulative fines passing through the screen is 0.5% by weight of the sample. This value is obtained by plotting on a graph the mass of fines obtained as a function of the force applied to the adsorbent bed and by interpolating to 0.5% by mass of cumulative fines. The mechanical bulk crushing strength is typically between a few hundred kPa and a few tens of MPa and generally between 0.3 MPa and 4 MPa. The accuracy is conventionally less than 0.1 MPa.

Determination of the Zeolite Fractions of the Zeolite Adsorbents:

The nature and amount of the various zeolite fractions are determined by X-ray diffraction analysis, known to those skilled in the art by the abbreviation XRD. This analysis is performed on a Brüker brand machine, and the amount of zeolite fractions is then evaluated using the TOPAS software from the company Brüker.

Micropore Volume:

The crystallinity of the agglomerates is also evaluated by measuring their micropore volume and comparing it to that of a suitable reference (100% crystalline zeolite under identical cationic treatment conditions or theoretical zeolite). This micropore volume is determined from the adsorption isotherm of a gas, such as nitrogen, at its liquefaction temperature. Prior to the adsorption, the zeolite adsorbent is degassed between 300° C.-450° C. for a period of 9 hours to 16 hours, under vacuum (P<6.7×10$^{-4}$ Pa). Measurement of the nitrogen adsorption isotherm at 77 K is then performed on a machine ASAP 2010 M type from Micromeritics, taking at least 35 measurement points at relative pressure ratios $P/P_0$ of between 0.002 and 1. The micropore volume is determined according to Dubinin and Raduskevitch from the isotherm obtained, by applying standard ISO 15901-3: 2007. The micropore volume evaluated according to Dubinin and Raduskevitch is expressed in cm$^3$ of liquid adsorbate per gram of adsorbent. The measuring uncertainty is ±0.003.

Loss on Ignition of the Zeolite Adsorbents:

The loss on ignition is determined in an oxidative atmosphere, by calcination of the sample in air at a temperature of 950° C.±25° C., as described in standard NF EN 196-2 (April 2006). The measurement standard deviation is less than 0.1%.

Characterization of the Liquid-Phase Adsorption by Breakthrough:

The technique used to characterize the liquid-phase adsorption of molecules on a porous solid is the "breakthrough" technique, described by Ruthven in "Principles of Adsorption and Adsorption Processes" (Chapters 8 and 9, John Wiley & Sons, 1984) which defines the technique of breakthrough curves as the study of the response to the injection of a grade of adsorbable constituents. Analysis of the mean outlet time (first moment) of the breakthrough curves gives information regarding the amounts adsorbed and also makes it possible to evaluate the selectivities, i.e. the separation factor, between two adsorbable constituents. Injection of a non-adsorbable constituent used as tracer is recommended for estimating the non-selective volumes. Analysis of the dispersion (second moment) of the breakthrough curves makes it possible to evaluate the equivalent height of theoretical plates, based on the representation of a column by a finite number of ideally stirred hypothetical reactors (theoretical stages), which is a direct measurement of the axial dispersion and of the resistance to matter transfer of the system.

EXAMPLES

Preparation of the Zeolite Adsorbents

A homogeneous mixture is prepared and 800 g of zeolite NaX crystals are agglomerated according to the procedure described in patent application FR 2 999 098 (synthesis of Example B) with 105 g of kaolin (expressed as calcined equivalent) and 45 g of colloidal silica sold under the trade name Klebosol®30 (containing 30% by weight of $SiO_2$ and 0.5% of $Na_2O$) with an amount of water which allows extrusion of the mixture. The extrudates are dried, crushed so as to recover grains with a number mean diameter equal to 0.5 mm, and then calcined at 550° C. under a stream of nitrogen for 2 hours.

200 g of agglomerates obtained are placed in a glass reactor equipped with a jacket regulated at a temperature of 100° C.±1° C., 1.5 L of an aqueous sodium hydroxide solution with a concentration of 2.5 M are then added and the reaction medium is left stirring for a period of 4 hours.

The agglomerates are then washed in 3 successive washing operations with water followed by emptying of the reactor. The washing efficiency is ensured by measuring the final pH of the washing waters, between 10.0 and 10.5.

Example 1: Barium and Potassium Cation Exchange

The sodium cations of the agglomerates obtained are exchanged with barium and potassium ions by means of an aqueous 0.5M solution of potassium chloride and of barium chloride at 95° C. in 4 steps. The potassium chloride and barium chloride concentrations in the solution are adapted so as to achieve the targeted barium and potassium contents in the adsorbent and thus the $K_2O/(K_2O+BaO+Na_2O)$ mole ratios targeted (FIG. 1). In particular, a $K_2O/(K_2O+BaO+Na_2O)$ mole ratio of 8.0% is achieved with a aqueous solution of 0.40M barium chloride and of 0.10M potassium chloride. In each step, the ratio of the volume of solution to the mass of solid is 20 mL/g and the exchange is continued for 3 hours each time. Between each exchange, the solid is washed several times so as to free it of the excess salt. The agglomerates are then dried at 80° C. for 2 hours and finally activated at 250° C. for 2 hours under a stream of nitrogen.

The loss on ignition measured, as described previously, is 5.6%±0.1% for each sample. The degree of barium+potassium exchange of the agglomerates calculated from the elemental analyses of the barium and sodium oxides by X-ray fluorescence as described in the characterization techniques is 99.7±0.2%. In particular, for the $K_2O/(K_2O+BaO+Na_2O)$ mole ratio of 8.0%, the content of sodium oxide $Na_2O$ is of 0.05% by weight relative to the total mass of the adsorbent, the content of barium oxide BaO is of 35.15% by weight relative to the total mass of the adsorbent and the content of potassium oxide $K_2O$ is of 1.89% by weight relative to the total mass of the adsorbent.

Example 2: Breakthrough Test

A breakthrough test (frontal chromatography) is then performed on the agglomerates obtained in Example 1 to evaluate their efficiency. The amount of adsorbent used for this test is about 30 g.

The procedure of obtaining the breakthrough curves is as follows:
 Filling of the column with the screen and insertion in the test bench.
 Filling with the solvent (toluene) at room temperature.
 Gradual increase to the adsorption temperature under a stream of solvent (2 cm³/min).
 Injection of solvent at 2 cm³/min when the adsorption temperature is reached.
 Solvent/feed permutation to inject the feed (2 cm³/min).
 Injection of the feed is then maintained for a time sufficient to reach thermodynamic equilibrium.
 Collection of the breakthrough retainings in a single flask followed by analysis of the composition of the retainings by GC.

The pressure is sufficient for the feed to remain in the liquid phase, i.e. 1 MPa. The adsorption temperature is 175° C. The composition of the feed used for the tests is as follows:
 para-Xylene: 18% by weight
 meta-Xylene: 18% by weight
 ortho-Xylene: 18% by weight
 Ethylbenzene: 18% by weight
 pare-Diethylbenzene: 18% by weight
 Isooctane: 10% by weight (this is used as tracer for estimating the non-selective volumes and does not participate in the separation)

The selectivities of the compounds in pairs, written as the binary selectivities $\alpha_{i/k}$, are calculated from the amounts adsorbed $q_i$ and $q_k$ of the compounds i and k, the latter being determined by material balance from the analysis of the composition of the breakthrough retainings and the composition of the feed (feed in which the mass fraction of the compounds i and k is $y_i$ and $y_k$):

$$\text{Section 1: } K_{ss} < m_1 \delta_1 < +\infty \tag{8}$$
$$\text{Section 2: } K_{wk} < m_2 \delta_2 < K_{sk}$$
$$\text{Section 3: } K_{wk} < m_3 \delta_3 < K_{sk}$$
$$\text{Section 4: } -\frac{\epsilon_p \delta_4}{\sigma(1-\epsilon_p)} < m_4 \delta_4 < K_{ww}$$

Evaluation of the potential of these adsorbents during the simulated counter-current operation is done on the basis of the equilibrium theory applied to multi-constituent systems with constant selectivities as described by Mazotti, Storti and Morbidelli in Robust Design of Countercurrent Adsorption Separation Processes: 2. Multicomponent Systems, AlChE Journal November 1994 Volume 40, No. 11. In particular, reference is made here to equation 8, which describes the conditions to be satisfied regarding the reduced delivery rates $m_j$ for the 4 sections (j=1 to 4) of a counter-current separation unit as represented schematically in FIG. 1 of the cited article to obtain total separation.

$$a_{i/k} = \frac{q_i y_k}{q_k y_i}.$$

This equation 8 makes reference to the adsorptivities $K_i$ of the various constituents and also to the parameter $\delta_j$ of each section j defined by equation 7:

$$\delta_j = \sum_{i=1}^{NC} K_i y_i^j \ (j=1,\ldots,4) \tag{7}$$

It should be noted here that, by definition, the binary selectivity $\alpha_{i/k}$ between compounds i and k is equal to the ratio of the adsorptivities $K_i/K_k$.

The reduced delivery rate for each section of the unit is defined as being the ratio of the delivery rate of the liquid phase to the delivery rate of the adsorbed phase. Equation 8 indicates what the limit reduced delivery rates are for each section. In a 4-section counter-current separation unit, the feed delivery rate corresponds to the difference between the delivery rate in zone 3 and the delivery rate in zone 2.

Therefore, when it is desired to evaluate the maximum productivity which can be achieved with a given adsorbent, it is sought to evaluate the maximum amount of feed that may be treated, i.e. to evaluate the difference between the maximum delivery rate in zone 3 and the minimum delivery rate in zone 2. The performance qualities may be compared in terms of maximum productivity of two adsorbents by comparing their maximum reduced delivery rate of feed determined from the reduced delivery rates of zones 2 and 3, respectively $m_2$ and $m_3$, according to the relationship: $\max(m_{Feed})=\max(m_3)-\min(m_2)$.

If a system with constant selectivities is considered, the composition of the liquid phase that gives the greatest stress in zone 2 and in zone 3 is the composition of the liquid phase at the point of injection of the feed into the unit. Specifically, from this point, the concentration of para-xylene, which is the most adsorbed compound, increases in the direction of circulation of the solid in zone 2, and decreases in the direction of circulation of the liquid in zone 3. The composition of this point may be approximated to the composition of the feed to be treated, and it is this composition that will be used to evaluate the term $\delta_2$ and $\delta_3$ of equation 8. The terms $\delta_2$ and $\delta_3$ are defined by equation 7 mentioned above. For each adsorbent, this reduced delivery rate max($m_{Feed}$) is calculated from the binary selectivity values measured experimentally and represented in FIG. 1 as a function of the $K_2O/(K_2O+BaO+Na_2O)$ mole ratio (FIG. 1). It is seen that the reduced delivery rate max($m_{Feed}$) is improved for a $K_2O/(K_2O+BaO+Na_2O)$ mole ratio of between 8.0% and 8.6%.

The invention claimed is:

1. A zeolite adsorbent comprising:
   zeolite X crystals; and
   barium, potassium and sodium,
   wherein the $K_2O/(K_2O+BaO+Na_2O)$ mole ratio is between 0.08 and 0.086, and
   wherein the content of sodium oxide $Na_2O$ is less than 0.3% by weight relative to the total mass of the adsorbent.

2. The zeolite adsorbent according to claim 1, further comprising a non-zeolite phase.

3. The zeolite adsorbent according to claim 1, wherein the total content of alkali metal or alkaline-earth metal ion oxides other than barium oxide (BaO), potassium oxide ($K_2O$) and sodium oxide ($Na_2O$) is less than 1% by weight relative to the total mass of the adsorbent.

4. The zeolite adsorbent according to claim 1, wherein the zeolite X crystals have an Si/Al atomic ratio of between 1.00 and 1.50.

5. The zeolite adsorbent according to claim 1, having wherein the adsorbent has a number mean diameter of between 0.2 mm and 2 mm.

6. The zeolite adsorbent according to claim 1, wherein the zeolite X crystals have a number mean diameter of less than or equal to 1.5 µm.

7. The zeolite adsorbent according to claim 1, wherein the adsorbent has a loss on ignition, measured at 950° C. according to standard NF EN 196-2, of between 4.0% and 7.7% by weight.

8. The zeolite adsorbent according to claim 1, wherein the zeolite X crystals are present in an amount of at least 80% by weight relative to the total weight of the adsorbent.

9. A process for preparing an adsorbent according to claim 1, comprising at least the steps of:
   a) agglomerating zeolite X crystals with a binder, and forming agglomerate, followed by drying and calcination,
   b) optional zeolitization of the binder,
   c) cation exchange of the agglomerate by placing in contact with a solution of barium ions, or of potassium ions, or of barium ions and potassium ions,
   d) cation exchange with potassium when the exchange step c) is performed with a solution of barium ions alone, or cation exchange with barium when the exchange step c) is performed with a solution of potassium ions alone,
   e) followed by washing and drying of the product thus treated, and
   f) activation of the zeolite adsorbent thus obtained.

10. The process according to claim 9, wherein the binder used in step a) contains at least 80% by weight of zeolitizable clay and a source of silica, and wherein the process comprises a step b) of zeolitization of said zeolitizable binder via the action of an alkaline basic solution.

11. The process according to claim 9, wherein the zeolite X used in step a) comprises a hierarchically porous type X FAU zeolite.

12. A process for recovering para-xylene from isomer fractions of aromatic hydrocarbons containing 8 carbon atoms in a liquid phase, comprising:
   contacting an isomer fraction of aromatic hydrocarbons containing 8 carbon atoms with the adsorbent according to claim 1 in a liquid phase in the presence of a desorbent.

13. The process according to claim 12, which is conducted on a simulated moving bed.

14. A process for recovering para-xylene from isomer fractions of aromatic hydrocarbons containing 8 carbon atoms in a gaseous phase, comprising:
   contacting an isomer fraction of aromatic hydrocarbons containing 8 carbon atoms with the adsorbent according to claim 1 in a gaseous phase in the presence of a desorbent.

15. A process for separating polyhydric alcohols, comprising:
   contacting polyhydric alcohols with the adsorbent according to claim 1.

16. A process for separating substituted toluene isomers, comprising:
   contacting substituted toluene isomers with the adsorbent according to claim 1.

17. A process for separating cresols, comprising:
   contacting cresols with the adsorbent according to claim 1.

18. A process for separating aromatic C8 isomer fractions, comprising:
   contacting an aromatic C8 isomer fraction with the zeolite adsorbent according to claim 1.

* * * * *